United States Patent
Achari et al.

(10) Patent No.: US 6,677,346 B1
(45) Date of Patent: Jan. 13, 2004

(54) METHODS COMPRISING INTRANASAL MORPHINE

(75) Inventors: Raja G. Achari, Millington, NJ (US); Charanjit R. Behl, Hauppauge, NY (US); Jorge C. deMeireles, Syosset, NY (US); Ramneik Dua, Central Islip, NY (US); Vincent D. Romeo, Massapequa Park, NY (US); Anthony P. Sileno, Brookhaven, NY (US)

(73) Assignee: Nastech Pharmaceutical Company Inc., Bothell, WA (US)

( * ) Notice: Subject to any disclaimer, the term of this patent is extended or adjusted under 35 U.S.C. 154(b) by 71 days.

(21) Appl. No.: 09/594,916

(22) Filed: Jun. 15, 2000

Related U.S. Application Data (62) Division of application No. 09/334,537, filed on Jun. 16, 1999.

(51) Int. Cl.⁷ .................... A61K 31/44; A61K 9/24; A61K 9/58; A61K 9/14; A61K 9/50
(52) U.S. Cl. ............. 514/282; 424/434; 424/489; 424/494; 424/499
(58) Field of Search ................. 514/282; 424/434, 424/489, 494, 499

(56) References Cited

U.S. PATENT DOCUMENTS

| | | |
|---|---|---|
| 4,464,378 A | 8/1984 | Hussain |
| 5,202,128 A | 4/1993 | Morella et al. |
| 5,629,011 A | 5/1997 | Illum |
| 5,756,483 A | 5/1998 | Merkus |
| 5,880,132 A | 3/1999 | Hill |
| 5,942,251 A | 8/1999 | Merkus |

FOREIGN PATENT DOCUMENTS

WO    WO 82/03768    11/1982

OTHER PUBLICATIONS

The Merck Index (Twelfth Edition), p. 1074–1075.*
The Merck Index (Twelfth Edition), p. 126.*
"Current and Practical Compounding Information for the Pharmacist: Compounding Nasal Preparations", 1998, Paddocklabs Inc., www.paddocklabs.com.*
Banker et al., *Modern Pharmaceutics*, Ch. 2, p. 40 (1979).

* cited by examiner

*Primary Examiner*—Zohreh Fay
*Assistant Examiner*—Brian-Yong S. Kwon
(74) *Attorney, Agent, or Firm*—Graybeal Jackson Haley LLP

(57) ABSTRACT

The present invention relates to a pharmaceutical formulation for intranasal administration comprising morphine or pharmaceutically acceptable salt thereof at a pH from about 3.0 to about 7.0. Such formulations provide enhanced absorption of morphine or pharmaceutically acceptable salts thereof. In one embodiment, the present invention provides a method for eliciting an analgesic or anesthetic response in a mammal which includes nasally administering a therapeutically effective amount of morphine or pharmaceutically acceptable salt thereof at a pH from about 3.0 to about 7.0.

13 Claims, 8 Drawing Sheets

FIG. 1

Plots of Average Free Morphine Plasma Conc. vs. Time for Morphine Sulfate Nasal Spray, Lot No. 98083A

FIG. 2

Plots of Average Free Morphine Plasma Conc. vs. Time for Morphine Sulfate Nasal Spray, Lot No. 99002A

FIG. 3

Plots of Average Free Morphine Plasma Conc. vs Time for Morphine Sulfate Nasal Spray, Lot No. 99024A and 99020A

FIG. 4

Plots of Average Free Morphine Plasma Conc. vs. Time for Morphine Sulfate Nasal Spray, Not No. 99006A

Plots of Average Free Morphine Plasma Conc. vs. Time for Morphine Sulfate Nasal Spray, Lot No. 99029A

FIG. 8

Plots of Average Free Morphine Plasma Conc. vs. Time for Morhpine Sulfate Nasal Spray, Lot No. 99022A FIG. 9
Plots of Average Free Morphine Plasma Conc. vs. Time for Morhpine Sulfate Nasal Spray, Lot No. 99015A

FIG. 10

Plots of Average Free Morphine Plasma Conc. vs. Time for Morhpine Sulfate Nasal Spray, Lot No. 99014A

FIG. 11

Plots of Average Free Morphine Plasma Conc vs. Time for Morphine Sulfate Nasal Spray, Lot No. 99025A

FIG. 12

Plots of Average Free Morphine Plasma Conc. vs. Time for Morhpine Sulfate Nasal Spray, Lot No. 99008A FIG. 13
Plots of Average Free Morphine Plasma Conc. vs. Time for Morhpine Sulfate Nasal Spray, Lot No. 99007A
• SLS (1%)
• Oleic Acid (0.5%)
• Tween 20 (5%)

METHODS COMPRISING INTRANASAL MORPHINE

CROSS REFERENCE TO RELATED APPLICATIONS

This application is a divisional application of U.S. application Ser. No. 09/334,537, filed on Jun. 16, 1999.

FIELD OF THE INVENTION

The present invention relates to pharmaceutical formulations for intranasal administration comprising morphine or pharmaceutically acceptable salt thereof at a pH from about 3.0 to about 7.0. The formulations of the present invention provide enhanced absorption useful for eliciting analgesic or anesthetic responses in mammals.

BACKGROUND OF THE INVENTION

The compound morphine or (−)7,8-didehydro-4,5α-epoxy-17-methylmorphinan-3,6α-diol, is a phenanthrene derivative that exhibits the following general structure:

Structure A (see page before claims)

Morphine is a centrally acting narcotic analgesic that acts as an agonist primarily at mu, kappa and perhaps delta receptors in the central nervous system. By acting on these receptors, morphine causes analgesia and anesthesia as a result of a receptor-mediated central action on pain perception, together with a receptor-medicated modulatory effect on the central transmission of noxious sensation. Some side effects caused by morphine include drowsiness, respiratory depression and euphoria.

Various morphine salts are known in the pharmaceutical arts. For example, morphine sulfate is one of the most commonly prescribed morphine formulations. Other morphine salts such as morphine tartrate and morphine lactate are disclosed in U.S. Pat. No. 5,880,132 issued to Hill and U.S. Pat. No. 5,378,474 to Morella et al. for the treatment and prevention of pain or nociception. Some polar formulations of morphine including morphine-3-glucuronide and morphine-6-glucuronide are disclosed in U.S. Pat. No. 5,629,011 to Illum.

Morphine has been used for a variety of clinical indications. Some examples of such indications include analgesia, for treatment of acute and chronic pain, anesthesia during surgery and to allay anxiety during acute pulmonary edema.

Several delivery routes have been utilized for administering morphine. These routes include oral, injectable, buccal and intranasal administration. For example, oral and injectable morphine sulfate are commonly prescribed for cancer pain. Oral and injectable morphine sulfate are available from Roxane Pharmaceuticals Inc., USA.

Other more desirable delivery routes have been investigated. For example, intranasal delivery of morphine has shown potential for rapid onset and duration of action. Further, intranasal administration offers potential for minimal delays in absorption, is not as invasive as intravenous delivery and achieves therapeutically effective amounts of the drug in plasma For example, intranasal delivery of morphine is disclosed in U.S. Pat. No. 5,629,011 to Illum and U.S. Pat. No. 4,464,378 to Hussain for the treatment of chronic and acute pain. The entire disclosure of U.S. Pat. No. 5,629,011 and U.S. Pat. No. 4,464,378 is herein incorporated by reference.

In considering the intranasal delivery of drugs, the pharmacokinetics thereof are often considered For example, ionization of a drug is believed to directly influence membrane penetration of the drug, and therefore, the absorption potential of the drug into the blood stream. In particular, the ionization of a drug and therefore its absorption potential, is largely determined by the drug's dissociation constant, $pK_a$, as well as the pH of the solution in which the drug is dissolved. As reported by Mayersohn in *Modern Pharmaceutics*. Banker & Rhodes, 1979, Ch. 2, Pg. 40, basic compounds are best absorbed from alkaline solutions where $pH>pK_a$. Thus, it is generally believed that formulations for delivering basic drugs, in particular intranasal formulations, are best absorbed into the bloodstream when the basic drug is prepared in a formulation solution having a pH above the dissociation constant of the drug. Therefor, a basic drug, such as morphine, would best be absorbed in a basic solution since it would be in its unionized state.

For example, morphine is known to be a basic drug with a $pK_a$ of about 8. In order to provide effective membrane penetration and absorption through intranasal delivery, heretofore it has been understood that morphine sulfate should be formulated in a basic solution having a formulation pH greater than about 7.0.

Intranasal formulations of morphine sulfate at pH levels below 7.0 would have greater than about 90% of the drug ionized. Such ionization of the drug is believed to lead to poor intranasal absorption. Therefore, several morphine spray formulations are prepared at a pH between 7–8.0. For example, U.S. Pat. No. 5,629,011 to Illum and U.S. Pat. No. 4,464,378 to Hussain disclose morphine formulations for intranasal spray delivery prepared at a pH of 7.2±0.2. These references discuss adding different absorption enhancers to achieve therapeutically effective amounts of morphine upon intranasal administration at such pH range.

Accordingly, efforts have been directed to adding absorption enhancers to intranasal formulations of morphine. Some examples of absorption enhancers include chitosan microspheres, cationic polymers, bioadhesive agents, surface active agents, fatty acids, chelating agents, mucolytic agents and cyclodextrin.

Based on the foregoing, there is a need for morphine formulations that provide enhanced absorption upon intranasal administration. Accordingly, the present invention provides a pharmaceutical formulation for intranasal administration comprising morphine or pharmaceutically acceptable salt thereof at a pH from about 3.0 to about 7.0. Such formulations provide therapeutically effective amounts of morphine for eliciting analgesic and anesthetic responses.

SUMMARY OF THE INVENTION

The present invention provides a pharmaceutical formulation for intranasal administration comprising morphine or pharmaceutically acceptable salt thereof at a pH from about 3.0 to about 7.0.

In one embodiment, the present invention provides a method for eliciting an analgesic or anesthetic response in a mammal comprising nasally administering a therapeutically effective amount of morphine or pharmaceutically acceptable salt thereof at a pH from about 3.0 to about 7.0.

In yet another embodiment, the present invention provides a method for eliciting an analgesic or anesthetic response in a mammal comprising nasally administering a therapeutically effective amount of morphine or pharmaceutically acceptable salt thereof at a pH from about 3.0 to about 7.0 to the mammal in combination with a nasal delivery system.

BRIEF DESCRIPTION OF THE DRAWINGS

FIG. 1 is a graph showing the plasma concentrations of free morphine when morphine sulfate was administered by the intranasal route. The formulation was at a pH of 4.0 and included sodium citrate dihydrate and citric acid as buffers.

DETAILED DESCRIPTION OF THE PREFERRED EMBODIMENTS

The present invention is a pharmaceutical formulation for intranasal administration comprising morphine or pharmaceutically acceptable salt thereof at a pH from about 3.0 to about 7.0. As used herein, "pharmaceutical formulation" is intended to include a pharmaceutically acceptable carrier which incorporates the active agent, i.e., morphine or pharmaceutically acceptable salt thereof. For purposes of the present invention, "pharmaceutical carrier" includes nasal sprays, nasal drops, gels, ointments, creams and the like.

Morphine is (−)7,8-didehydro-4,5α-epoxy-17-methylmorphinan-3,6α-diol. As used herein, "chemically modified equivalents" is intended to include compositions which may have a chemical structure that differs from morphine but which functions in a similar manner in the body, such as for example prodrugs, analogs, biologically active fragments and the like.

Chemically modified equivalents of morphine include oxymorphone or (−)4,5α-epoxy-3,14-dihyroxy-17-methylmorphinan-6-one, hydromorphone or (−)-4,5α-epoxy-3-hydroxy-17-methylmorphinan-6-one, levorphanol (−)-17-methylmorphinan-3-ol, nalbuphine or (−)-17-(cyclobutylmethyl)-4,5α-epoxymorphinan-3,5α, 14-triol, naloxone or (−)-17-allyl-4,5α-epoxy-3,14-dihydroxymorphinan-6-one, naltrexone or (−)-17-(cyclopropylmethyl)-4,5α-epoxy-3,14-dihydroxymorphinan-6-one, nalmefene or 6-desoxo-6-methylene-naltrexone, butorphanol or (−)-17-(cyclo-butylmethyl)-morphinan-3,14-diol, buprenorphine or (−)-17-(cyclopropylmethyl)-α-(1,1-dimethylethyl)-4,5-epoxy-18,19-dihydro-3-hydroxy-6-methoxy-α-methyl-6,14-ethenomorphinan-7-methanol, codeine, buprenophine, nalorphine, hydrocodone, oxycodone, butorphanol and pharmaceutically acceptable salts thereof.

The present invention includes pharmaceutically acceptable salts of morphine. Some examples of pharmaceutically acceptable salts include those salt-forming acids and bases which do not substantially increase the toxicity of the compound. Some examples of suitable salts include salts of alkali metals such as magnesium, potassium and ammonium. Salts of mineral acids include hydrochloric, hydriodic, hydrobromic, phosphoric, metaphosphoric, nitric and sulfuric acids, as well as salts of organic acids such as tartaric, acetic, citric, malic, benzoic, succinic, arylsulfonic, e.g. p-toluenesulfonic acids, and the like.

Particular examples of preferred pharmaceutically acceptable salts of morphine include morphine sulfate, morphine-6-sulfate, morphine-3-sulfate, morphine-6-glucuronide, morphine-3-glucuronide, morphine tartrate, morphine lactate, morphine hydrochloride and combinations thereof.

Applicants have unexpectedly found that pharmaceutical formulations including morphine or pharmaceutically acceptable salts thereof at a pH from about 3.0 to about 7.0 have enhanced or substantial absorption, even though the drug is mostly ionized. Further, it was found that at pH ranges where the drug is mostly ionized, the nasal absorption is pH sensitive. Preferably, morphine or pharmaceutically acceptable salt thereof is at a pH from about 4.0 to about 7.0, more preferably from about 4.0 to about 6.0, and most preferably, from about 5.0 to about 6.0.

As used herein, enhanced or substantial absorption includes increases in free morphine plasma concentrations by from about 5% to about 700%. Accordingly, a lower amount of drug can be used to achieve the same therapeutic levels that elicit an analgesic or anesthetic response.

Morphine, chemical equivalents of morphine and pharmaceutically acceptable salts of morphine may be obtained from various manufactures. For example, morphine sulfate is available from Roxane Pharmaceuticals Inc., USA.

The amount of pharmaceutically acceptable morphine salt, such as for example, morphine sulfate that can be used to make the formulations of the present invention can vary depending on the amount needed to achieve analgesia or anesthesia in the mammal. Preferably, the amount of morphine salt used is from about 0.01% to below about 50%, more preferably, from about 1% to below about 10%, and most preferably, from about 3% to below about 5% by weight of the total weight of the formulation (w/w). In any event, the practitioner is guided by skill and knowledge in the field, and the present invention includes without limitation amounts of morphine that are needed to achieve the described effect.

In the most preferred embodiment, morphine or pharmaceutically acceptable salt thereof is dissolved in a suitable solvent for intranasal administration. Suitable solvents include water, alcohol, glycerin, propylene glycol and the like. Preferably, the amount of solvent is sufficient to dissolve morphine aor pharmaceutically acceptable salt thereof. Most preferably, morphine is mixed at room temperature and at one atmosphere of pressure.

Intranasal Administration

The present invention includes nasally administering to the mammal a therapeutically effective amount of morphine or pharmaceutically acceptable salt thereof. As used herein, nasally administering or nasal administration includes administering morphine or pharmaceutically acceptable salt thereof to the mucous membranes of the nasal passage or nasal cavity of the mammal.

In one embodiment, the present invention provides a pharmaceutical formulation comprising a therapeutically effective amount of morphine or pharmaceutically acceptable salt thereof in combination with a nasal delivery system.

As used herein, pharmaceutical formulations include therapeutically effective amounts of morphine or pharmaceutically acceptable salt thereof. Such formulations can be administered, for example, as a nasal spray, nasal drop, suspension, gel, ointment, cream or powder. Administration of morphine formulations of the present invention may also take place using a nasal tampon or nasal sponge containing morphine or pharmaceutically acceptable salt thereof.

Nasal powder formulations can be made by mixing morphine or pharmaceutically acceptable salt thereof with an excipient, both possessing the desired particle size. Other methods to make a suitable powder formulation can be selected. First, a solution of morphine or pharmaceutically acceptable salt thereof is made, followed by precipitation, filtration and pulverization. It is also possible to remove the solvent by freeze drying, followed by pulverization of the powder in the desired particle size by using conventional techniques, known in the pharmaceutical arts. Powders can be administered using a nasal insufflator or any other suitable device.

Powders may also be administered in such a manner that they are placed in a capsule. The capsule is set in an inhalation or insufflation device. A needle is penetrated through the capsule to make pores at the top and the bottom of the capsule and air is sent to blow out the powder particles. Powder formulation can also be administered in a jet-spray of an inert gas or suspended in liquid organic fluids.

Morphine or pharmaceutically acceptable salt thereof can also be brought into a viscous base, using systems, conventionally used, for example natural gums, methylcellulose and derivatives, acrylic polymers (carbopol) and vinyl polymers (polyvinylpyrrolidone). Pharmaceutical formulations of the present invention may include, many other excipients, known from the pharmaceutical arts, such as preservatives, surfactants, co-solvents, adhesives, antioxidants, buffers, viscosity and absorption enhancing agents and agents to adjust the pH and osmolarity.

Preferably, morphine or pharmaceutically acceptable salt thereof is combined with a suitable delivery system for absorption across the nasal mucosa of a mammal. The nasal delivery system includes a pharmaceutically acceptable buffer, a thickening agent, a humectant, absorption enhancer and combinations thereof. Such nasal delivery system can take various forms including for example, aqueous solutions and non-aqueous solutions.

Aqueous solutions, include for example, aqueous gels, aqueous suspensions, aqueous liposomes, aqueous emulsions, aqueous microemulsions. Non aqueous solutions include, for example, non-aqueous gels, non-aqueous suspensions, non-aqueous liposomes, non-aqueous emulsions and non-aqueous microemulsions.

The various forms of the nasal delivery system set forth above can include a buffer to maintain the pH of morphine or pharmaceutically acceptable salt thereof, a pharmaceutically acceptable thickening agent, humectant, absorption enhancer and combinations thereof.

As stated above, Applicants have unexpectedly found that pharmaceutical formulations including morphine or pharmaceutically acceptable salts thereof have substantial absorption across the nasal mucosa at a pH from about 3.0 to about 7.0, even though morphine is in its ionized state. A suitable balance between the extent of drug absorption, dug stability, and drug solubility is selecting the pH of the nasal formulation. Preferably, morphine or pharmaceutically acceptable salt thereof is combined with a nasal delivery system at a pH from about 4.0 to about 7.0, more preferably from about 4.0 to about 6.0, and most preferably, from about 5.0 to about 6.0.

To maintain the formulation at a pH below about 7.0, the nasal delivery system may include a buffer with the desired buffer capacity as understood by those skilled in the art. The particular buffer, of course, can vary depending upon the particular nasal delivery system used, as well as the specific morphine formulation selected. Buffers that are suitable for use in the present invention include, for example, acetate, citrate, prolamine, carbonate and phosphate buffers and combinations thereof Some particularly preferred buffers are sodium citrate dihydrate and citric acid.

With respect to the non-aqueous and powder formulations set forth above, suitable forms of buffering agents can be selected so that when the formulation is delivered into the nasal cavity of a mammal, selected pH ranges are achieved therein upon contact with, e.g., the nasal mucosa.

As stated above, the pH of the pharmaceutical formulation should be from about 3.0 to about 7. Therefore, the pharmaceutical formulations of the present invention may include a pH adjusting agent. Examples of pH adjusting agents include trolamine, sulfuric acid, sodium hydroxide, diluted hydrochloric acid and the like. More preferably, the pH adjusting agent is added to the formulation as needed to maintain the pH at from about 4.0 to about 6.0, and most preferably, from about 5.0 to about 6.0.

The viscosity of the formulations of the present invention can be maintained at a desired level using a pharmaceutically acceptable thickening agent. Thickening agents that can be used in accordance with the present invention include for example, methyl cellulose, xanthan gum, carboxymethyl cellulose, hydroxypropyl cellulose, carbomer, polyvinyl alcohol, alginates, acacia, chitosans and combinations thereof. Such agents will also be used in the particulate formulations of the present invention. The concentration of the thickening agent will depend upon the agent selected and the viscosity desired. A most preferred thickening agent is polyvinyl alcohol. Such agent may be present in the formulation at a concentration of from about 0.1% to about 20% by weight of the total weight of the formulation.

The formulations of the present invention may also include a tolerance enhancer to reduce or prevent drying of the mucus membrane and to prevent irritation thereof. Suitable tolerance enhancers that can be used in the present invention include humectants, such as for example, sorbitol, mineral oil, vegetable oil, glycerol, glycerin, soothing agents, membrane conditioners, sweeteners and combinations thereof. The concentration of the tolerance enhancer(s) in the present formulations will also vary with the agent selected. The tolerance enhancer can be present in the delivery system in a concentration ranging from about 0.01% to about 20% by weight of the pharmaceutical formulation.

In order to enhance absorption of the morphine or pharmaceutically acceptable salt thereof through the nasal mucosa, a therapeutically acceptable absorption enhancer is added to the nasal delivery system. Suitable absorption enhancers that can be used in accordance with the present invention include, for example, sodium lauryl sulfate, sodium salicylate, oleic acid, lecithin, dehydrated alcohol, Tween, Span, polyoxyl 40 stearate, polyoxy ethylene 50 stearate, edetate disodium, propylene glycol, glycerol monooleate, fusieates, bile salts, octoxynol and combinations thereof. As used herein, Tween includes all Tweens such as Tween 20, Tween 40, Tween 60, Tween 80 and the like. Span include all Spans, such as Span 20, Span 40, Span 80 and the like. Suitable absorption enhancers include non-ionic, anionic and cationic surfactants. These absorption enhancers can be present in the delivery system in a concentration ranging from about 0.01% to about 50% by weight of the total formulation.

For example, preferred concentrations of sodium salicylate, sodium lauryl sulfate and edetate disodium can be from about 0.01% to about 5% by weight of the total formulation. Preferred concentrations of polyoxyl 40 stearate, lecithin, dehydrated alcohol, can be from about 0.1% to about 10% by weight of the total formulation. Preferred concentrations of oleic acid can be from about 0.01% to about 5% by weight of the total formulation. Preferred concentrations of propylene glycol and Tween 20 can be from about 0.1% to about 25% by weight of the total formulation.

The absorption enhancers of the present invention, increase plasma levels of free morphine above that observed without the absorption enhancer. Preferably, free morphine plasma concentrations are increased by from about 5% to about 700%. Accordingly, a lower amount of drug can be used to achieve the same therapeutic levels that elicit an analgesic or anesthetic response.

In the present invention other optional ingredients may also be incorporated into the nasal delivery system provided they do not interfere with the action of morphine or pharmaceutically acceptable salt thereof or significantly decrease the absorption of it across the nasal mucosa. Such ingredients can include, for example, pharmaceutically acceptable excipients and preservatives. The excipients that can be used in accordance with the present invention include, for example, bio-adhesives and/or swelling/thickening agents and combinations thereof.

To extend shelf life, preservatives can be added to the present formulations. Suitable preservatives that can be used with the present formulations include, for example, benzyl alcohol, parabens, thimerosal, chlorobutanol, benzalkonium and combinations thereof, with benzalkonium chloride being preferred. Typically, the preservative will be present in the formulations in a concentration of from about 0.001% up to about 5% by weight of the total formulation. The exact concentration of the preservative, however, will vary depending upon the intended use and can be easily ascertained by one skilled in the art.

Other ingredients which extend shelf life can be added such as for example, antioxidants. Some examples of antioxidants include sodium metabisulfite, potassium metabisulfite, ascorbyl palmitate and the like. Typically, the antioxidant will be present in the formulations in a concentration of from about 0.01% up to about 5% by weight of the total formulation.

It has been unexpectedly discovered that pharmaceutical formulations comprising morphine or pharmaceutically acceptable salt thereof at a pH from about 3.0 to about 7.0, achieve enhanced or substantial absorption and can be used to elicit analgesic or anesthetic effects as that observed with morphine at higher pH ranges. Further, it was found that at pH ranges where the drug is mostly ionized, the nasal absorption is pH sensitive.

Therapeutically Effective Amounts

As used herein, a therapeutically effective amount of morphine or pharmaceutically acceptable salt thereof is that amount effective to elicit an analgesic or anesthetic response. For example, morphine or pharmaceutically acceptable salt thereof can achieve the relief or palliation of acute, chronic or breakthrough pain. Preferably, morphine or pharmaceutically acceptable salt thereof is administered in an amount that limits the most common side effects such as respiratory depression, constipation and lethargy.

The minimal dosage of morphine or pharmaceutically acceptable salt thereof is the lowest dosage which elicits analgesia or anesthesia in the mammal. For example, morphine or pharmaceutically acceptable salt thereof can be administered at a minimal dosage of preferably from at least about 0.01 mg/kg to about 4 mg/kg of body weight, more preferably from at least about 1 mg/kg to about 4 mg/kg of body weight, and most preferably from at least about 2 mg/kg to about 4 mg/kg of body weight.

Maximal dosage for a mammal is the highest dosage which elicits analgesia or anesthesia which does not cause undesirable or intolerable side effects such as respiratory depression. In any event, the practitioner is guided by skill and knowledge in the field, and the present invention includes without limitation dosages which are effective to achieve the described effect in the mammal.

As used herein, analgesia or an analgesic response includes relieving pain in the mammal without causing loss of consciousness. Typically, morphine or pharmaceutically acceptable salt thereof can be used to elicit analgesia in the treatment of acute and chronic pain. Morphine or pharmaceutically acceptable salt thereof can also be used to produce anesthesia or an anesthetic response in the mammal. Typically, the mammal experiences loss of feeling or sensation, especially loss in pain sensation, to permit the performance of surgery or other painful procedures. Accordingly, when analgesia is induced the mammal loses consciousness.

Mammals include, for example, humans, as well as pet animals such as dogs and cats, laboratory animals, such as rats and mice, and farm animals, such as horses and cows.

The following examples are set forth to illustrate the formulations of the present invention, as well as the surprising results achieved therewith. These examples are provided for purposes of illustration only and are not intended to be limiting in any sense.

EXAMPLE 1

Morphine Sulfate Formulations pH 4.0–6.0

Figure 1:
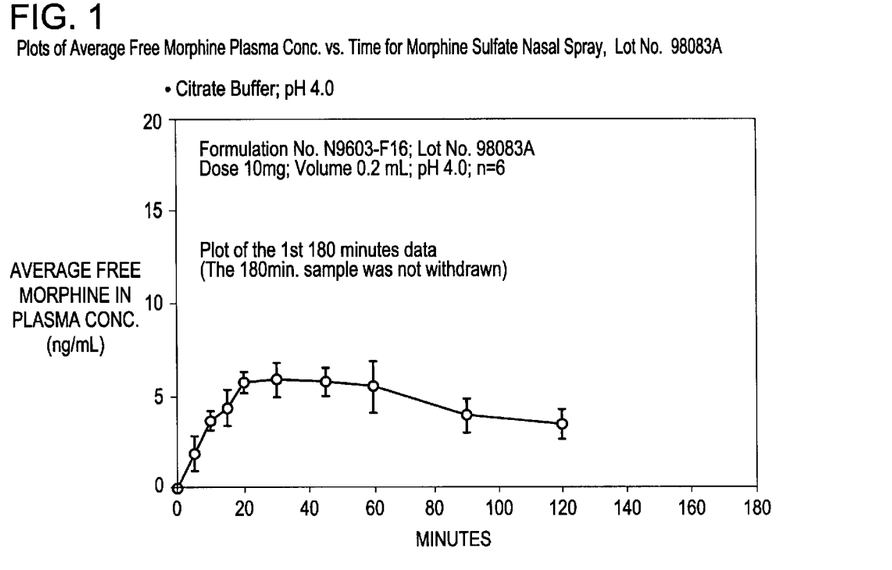
Figure 2:
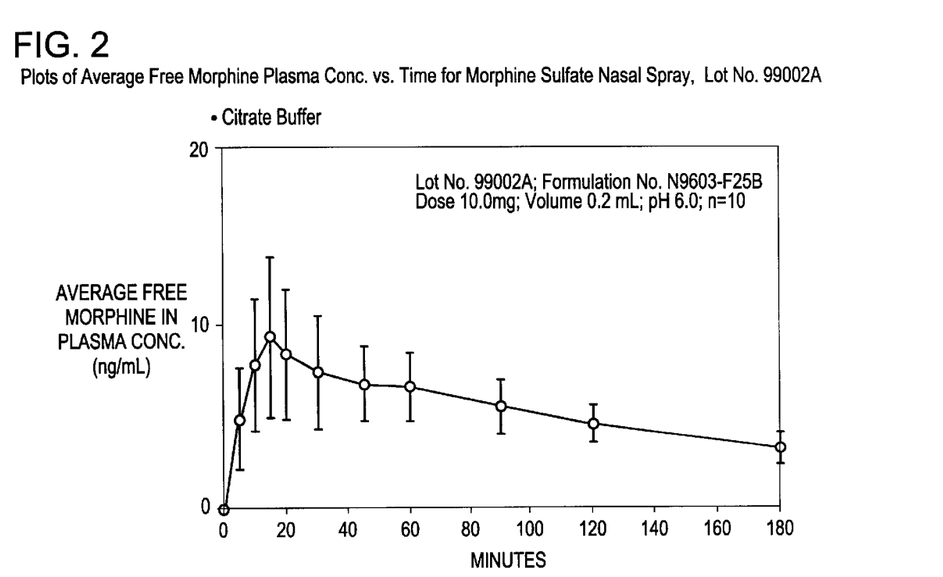
FIG. 2 is a graph showing the plasma concentrations of free morphine when morphine sulfate was administered by the intranasal route. The formulation was at a pH of 6.0 and included sodium citrate dihydrate as a buffer.

FIG. 1 is a graph showing the plasma concentrations of free morphine when 10 mg morphine sulfate was administered to healthy volunteers by the intranasal route using Formulation 1 (Table A). This formulation was at a pH of 4.0 and included sodium citrate dihydrate and citric acid as buffers. FIG. 2 is a graph showing the plasma concentrations of free morphine when 10 mg morphine sulfate was administered by the intranasal route using formulation 2 (Table B). This formulation was at a pH of 6.0 and included sodium citrate dihydrate as a buffer. The average peak concentrations ($C_{MAX}$) concentrations for intranasal Formulations 1 and 2 was 6.58 ng/ml and 10.3 ng/ml, respectively. Formulations 1 and 2 did not include an absorption enhancer. It was observed that the average $C_{MAX}$ for Formulation 2 was about 60% greater when the pH was raised to 6.0 as compared to the same 10 mg dose of morphine sulfate at a pH of 4.0 (Formulation 1). Also, the solubility of morphine sulfate at pH ranges 4.0 to 6.0 was found to be invariant with pH. These results were unexpected since morphine sulfate is predominately in its ionized state at pH ranges 4.0 to 6.0 and should be poorly absorbed and should not be pH dependent. By contrast, we found substantial absorption at pH ranges 4.0 to 6.0 where the drug is predominately ionized. Accordingly, nasal absorption is pH sensitive in this pH range.

EXAMPLE 2

Morphine Sulfate Formulation With Tween 20 Absorption Enhancer

Figure 3:
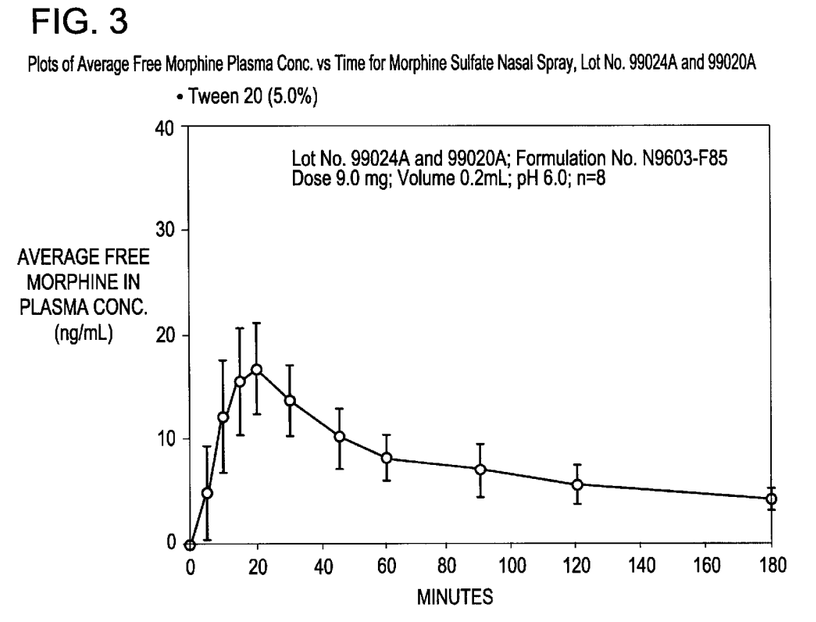
FIG. 3 is a graph showing the plasma concentrations of free morphine when morphine sulfate was administered by the intranasal route. The formulation was at a pH of 6.0 and included Tween 20 as the absorption enhancer.

FIG. 3 is a graph showing the plasma concentrations of free morphine when 9 mg morphine sulfate was administered to healthy volunteers by the intranasal route using Formulation 3. This formulation was at a pH of 6 and included about 5% Tween 20 (polysorbate 20) as the absorption enhancer (Table C). The average peak concentrations ($C_{MAX}$) concentration for intranasal Formulation 3 was 17.8 ng/ml. It was observed that use of Tween 20 at a pH of 6.0, enhanced the nasal absorption of morphine sulfate by about 73% beyond that observed using a citrate buffer and no enhancer, at a pH of 6.0, as in Formulation 2 (Table B). These results were unexpected since morphine sulfate is predominately in its ionized state at pH 4.0 to 6.0 and therefore it is expected that the absorption would be poor. By contrast, we found substantial absorption at pH ranges 4.0 to 6.0 where the drug is predominately ionized. Also, the addition of the absorption enhancer, such as Tween 20, increased intranasal absorption and peak plasma concentrations of morphine, even though a lower dosage of morphine sulfate was used.

EXAMPLE 3

Morphine Sulfate Formulation With Sodium Salicvlate Absorption Enhancers

Figure 4:
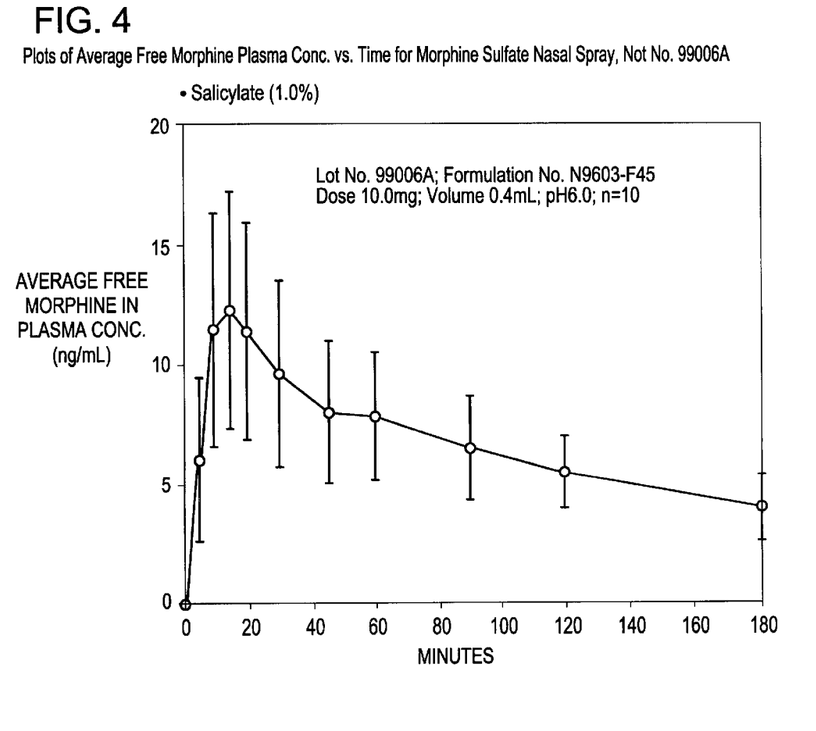
FIG. 4 is a graph showing the plasma concentrations of free morphine when morphine sulfate was administered by the intranasal route. The formulation was at a pH of 6.0 and included sodium salicylate as the absorption enhancer.

FIG. 4 is a graph showing the plasma concentrations of free morphine when 10 mg morphine sulfate was administered to healthy volunteers by the intranasal route using Formulation 4. This formulation was at a pH of 6.0 and included about 1% sodium salicylate as the absorption enhancer (Table D). The average peak concentrations ($C_{MAX}$) concentration for intranasal Formulation 4 was 13.3 ng/ml. It was observed that use of sodium salicylate at a pH of 6.0, enhanced the nasal absorption of morphine sulfate by about 30% beyond that observed using a citrate buffer and no enhancer at a pH of 6.0, as in Formulation 2 (Table B). These results were unexpected since morphine sulfate is predominately in its ionized state at pH 4.0 to 6.0 and therefore it is expected that the absorption would be poor and should not be pH dependent. By contrast, we found substantial absorption at pH ranges 4.0 to 6.0 where the drug is predominately ionized. Also, the addition of the absorption enhancer, such as sodium salicylate, increased intranasal absorption and peak plasma concentrations of morphine.

EXAMPLE 4

Figure 5:
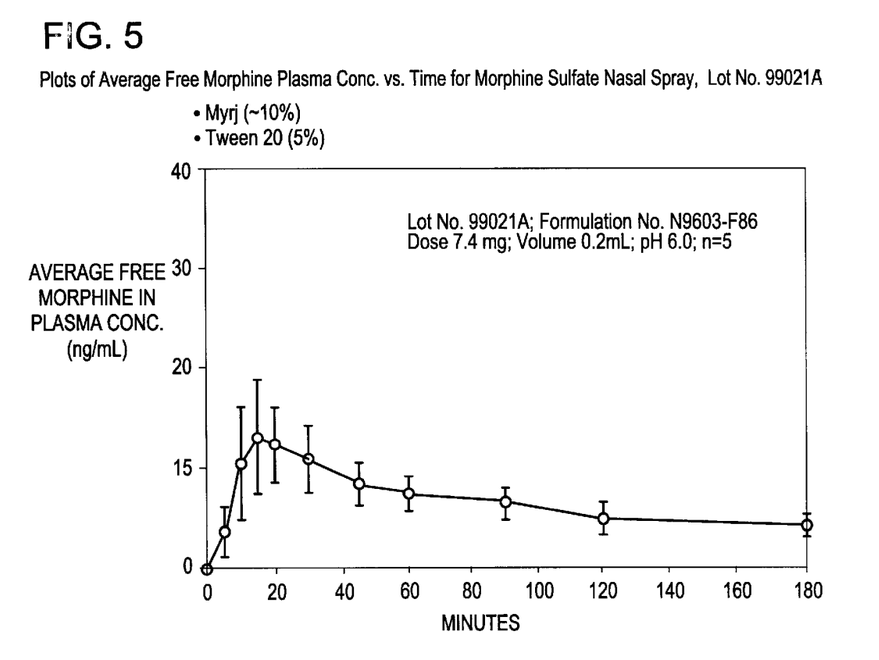
FIG. 5 is a graph showing the plasma concentrations of free morphine when morphine sulfate was administered by the intranasal route. The formulation was at a pH of 6.0 and included polyoxyl 40 stearate as the absorption enhancers.

Morphine Sulfate Formulations With Polyoxyl 40 Stearate Absorption Enhancers FIG. 5 is a graph showing the plasma concentrations of free morphine when 7.4 mg morphine sulfate was administered to healthy volunteers by the intranasal route using Formulation 5. This formulation was at a pH of 6.0 and included about 10% polyoxyl 40 stearate as the absorption enhancer (Table E). The average peak concentrations ($C_{MAX}$) concentration for intranasal Formulation 5 was 14.1 ng/ml. It was observed that use of polyoxyl 40 stearate at a pH of 6.0, enhanced the nasal absorption of morphine sulfate by about 37% beyond that observed using a citrate buffer and no enhancer at a pH of 6.0, as in Formulation 2 (Table B). Further, the use of polyoxyl 40 stearate was absorbed less than Formulation 3 which included Tween 20 in about 5% concentration at a pH of 6.0 These results were unexpected since morphine sulfate is predominately in its ionized state at pH 4.0 to 6.0 and therefore it is expected that the absorption would be poor. By contrast, we found substantial absorption at pH ranges 4.0 to 6.0 where the drug is predominately ionized. Also, the addition of the absorption enhancer, such as polyoxyl 40 stearate and Tween 20, increased intranasal absorption and peak plasma concentrations of morphine, even though a lower dosage of morphine sulfate was used.

EXAMPLE 5

Morphine Sulfate Powder Formulations With Tween 20 and Glyceryl-Monooleate

Figure 6:
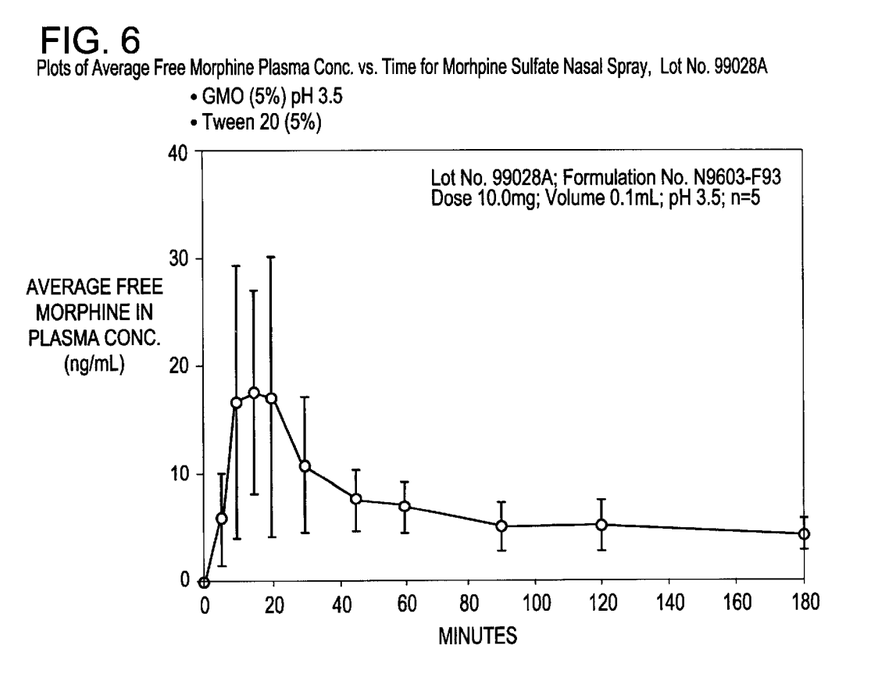
FIG. 6 is a graph showing the plasma concentrations of free morphine when morphine sulfate was administered by the intranasal route. The formulation was at a pH of 3.5 and included Tween 20 and glyceryl monooleate as the absorption enhancers.
Figure 7:
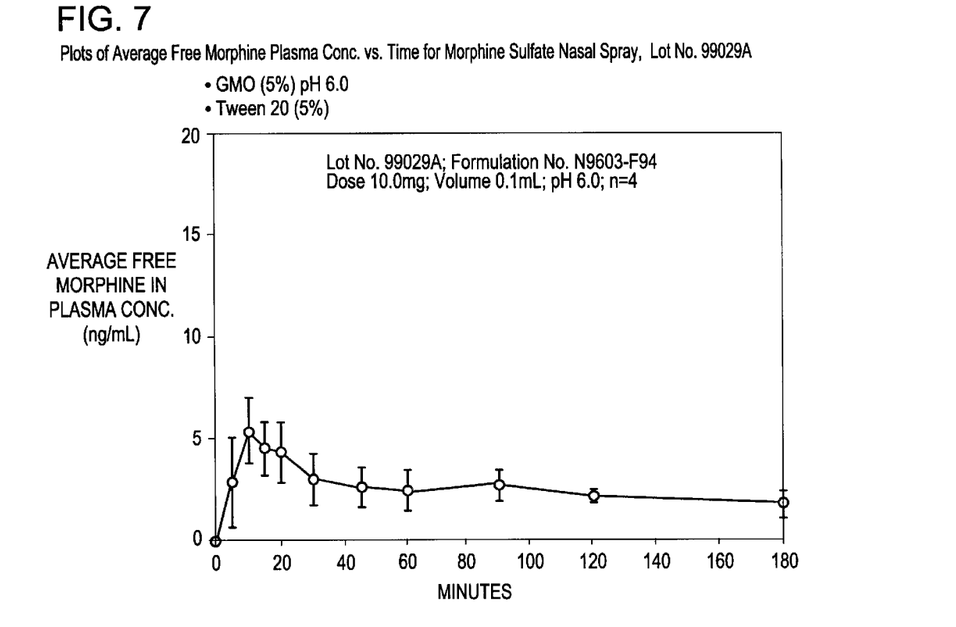
FIG. 7 is a graph showing the plasma concentrations of free morphine when morphine sulfate was administered by the intranasal route. The formulation was at a pH of 6.0 and included Tween 20 and glyceryl monooleate as the absorption enhancers.

FIG. 6 is a graph showing the plasma concentrations of free morphine when 10 mg morphine sulfate was administered to healthy volunteers by the intranasal route using Formulation 6 (Table F). The formulation was at a pH of 3.5 and included about 5% Tween 20 and about 5% glyceryl monooleate as the absorption enhancers. FIG. 7 is a graph showing the plasma concentrations of free morphine when 10 mg morphine sulfate was administered by the intranasal route using Formulation 7. This formulation was at a pH of 6.0 and included about 5% Tween 20 and about 5% glyceryl monooleate as the absorption enhancers. The average peak concentrations ($C_{MAX}$) concentrations for intranasal Formulations 6 and 7 was 19.0 ng/ml and 11.6 ng/ml, respectively. Referring to Formulation 6, the use of 5% glyceryl monooleate and 5% Tween 20 each provided comparable nasal absorption of morphine sulfate at a pH of 3.5, as compared to that observed using about 5.0% Tween 20 at a pH of 6.0 (Formulation 3). These findings were unexpected because the formulation at a pH of 3.5 should have provided much lower absorption of morphine. Further, referring to Formulation 7, use of 5% glyceryl monooleate and 5% Tween 20, each, enhanced the nasal absorption of morphine sulfate at a pH of 6.0 beyond that observed using a citrate buffer and no enhancer at a pH of 6.0, as in Formulation 2 (Table B). Further, absorption of Formulation 7 was not enhanced beyond that observed with Formulation 3, which includes 5% Tween 20 also at a pH of 6.0.

EXAMPLE 6

Figure 8:
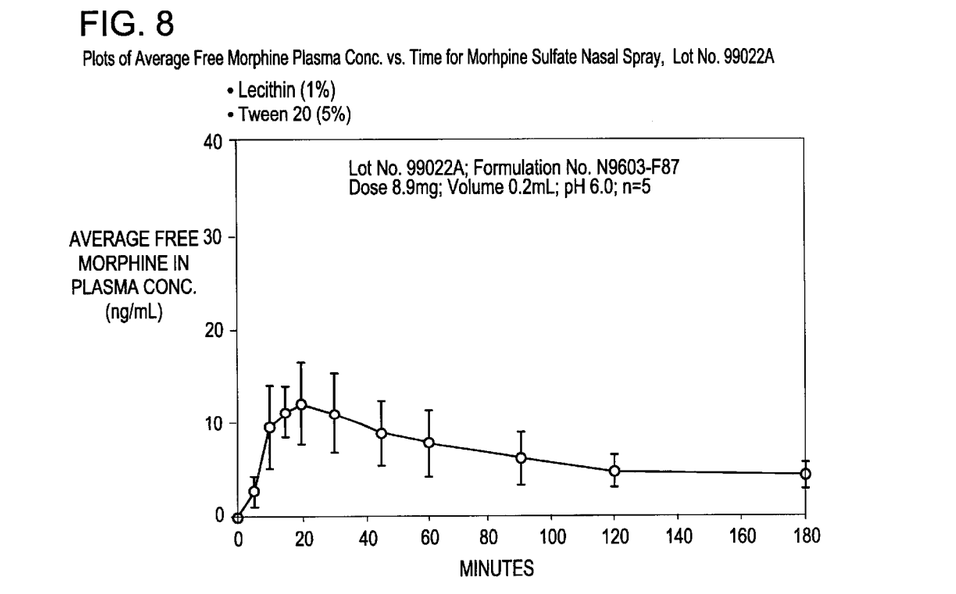
FIG. 8 is a graph showing the plasma concentrations of free morphine when morphine sulfate was administered by the intranasal route. The formulation was at a pH of 6.0 and included Tween 20 and lecithin as the absorption enhancers.
Figure 9:
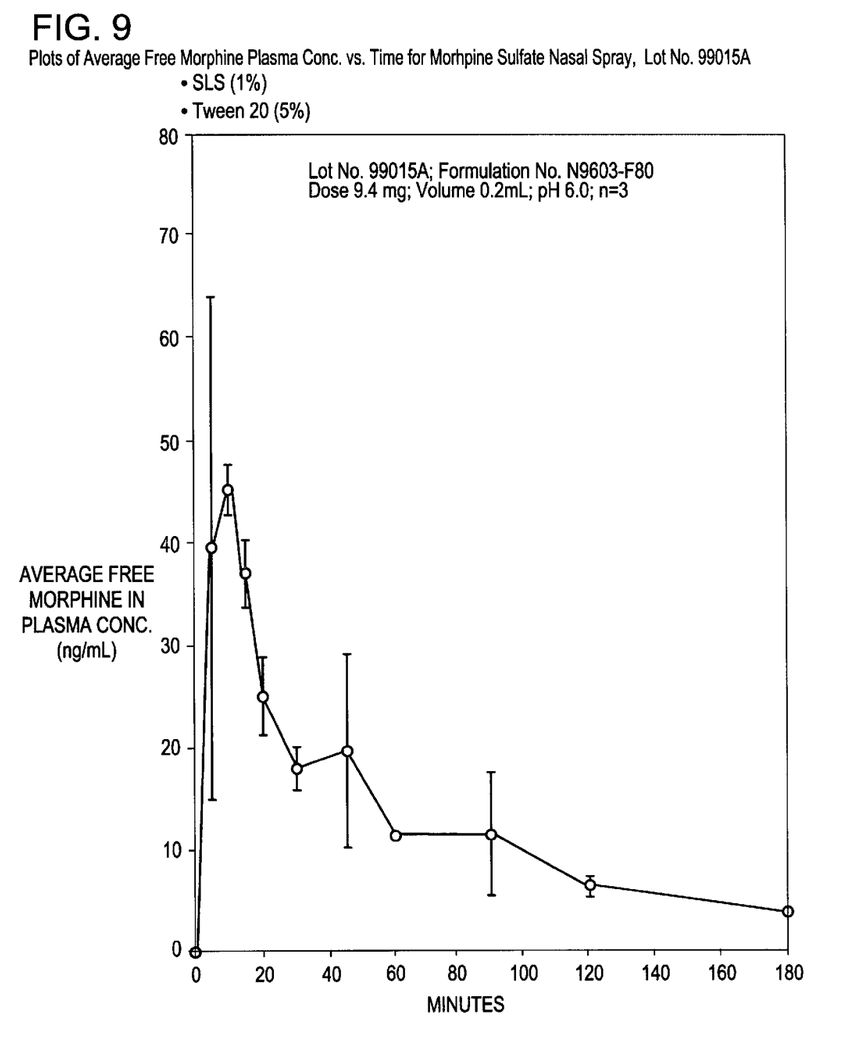
FIG. 9 is a graph showing the plasma concentrations of free morphine when morphine sulfate was administered by the intranasal route. The formulation was at a pH of 6.0 and included Tween 20 and sodium lauryl sulfate as the absorption enhancers.

Morphine Sulfate Formulations With Tween 20, Lecithin and/or Sodium Lauryl Sulfate Absorption Enhancers FIG. 8 is a graph showing the plasma concentrations of free morphine when 8.9 mg morphine sulfate was administered to healthy volunteers by the intranasal route using Formulation 8 (Table H). This formulation was at a pH of 6.0 and included about 5% Tween 20 and about 1% lecithin as the absorption enhancers. FIG. 9 is a graph showing the plasma concentrations of free morphine when 9.4 mg morphine sulfate was administered to healthy volunteers by the intranasal route using Formulation 9 (Table I). This formulation was at a pH of 6.0 and included about 5% Tween 20 and 1% sodium lauryl sulfate as the absorption enhancers. The average peak concentrations ($C_{MAX}$) concentrations for intranasal Formulations 8 and 9 was 13.1 ng/ml and 52.2 ng/ml, respectively. Referring to FIG. 8, use of 1% lecithin and 5% Tween 20 enhanced the nasal absorption of morphine sulfate at a pH of 6 (Formulation 8) beyond that observed using a citrate buffer at a pH of 6.0, as in Formulation 2 (Table B). Formulation 8 did not enhance the absorption beyond that observed with Formulation 3, which includes 5% Tween 20 also at a pH of 6.0. Referring to FIG. 9, use of about 1% sodium lauryl sulfate and 5% Tween 20 at a pH of 6.0 (Formulation 9), enhanced the nasal absorption of morphine sulfate at a pH of 6 beyond that observed with Formulation 3, which includes 5% Tween 20 also at a pH of 6.0. Such enhanced absorption was about 300% when the average peak concentrations for Formulations 3 and 9 are compared. These results were unexpected since morphine sulfate is predominately in its ionized state at pH 4.0 to 6.0 and therefore it is expected that the absorption would be poor. By contrast, we found substantial absorption at pH ranges 4.0 to 6.0 where the drug is predominately ionized.

EXAMPLE 7

Figure 10:
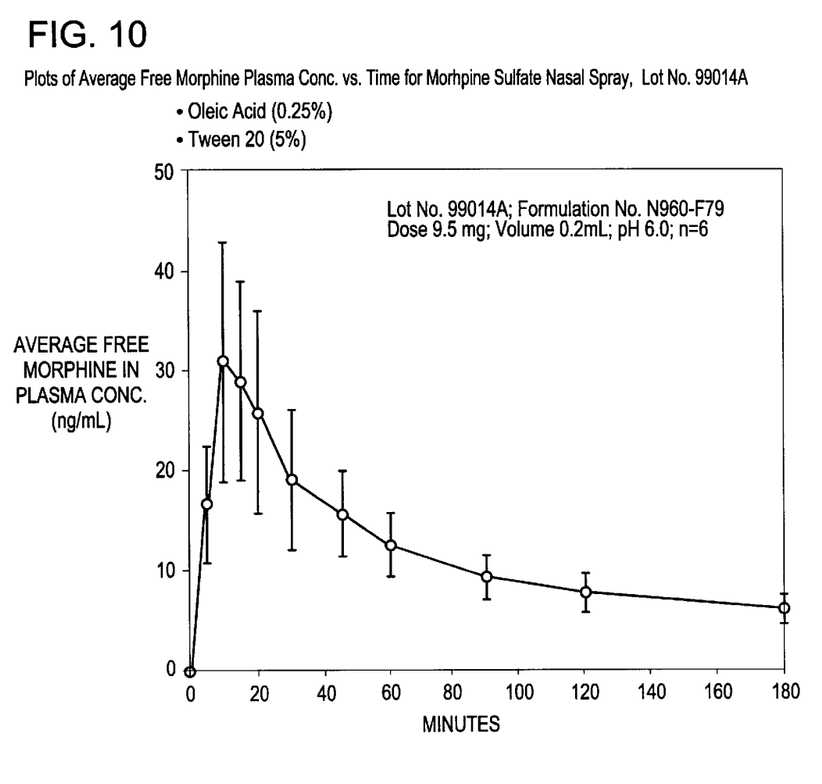
FIG. 10 is a graph showing the plasma concentrations of free morphine when morphine sulfate was administered by the intranasal route. The formulation was at a pH of 6.0 and included Tween 20 and oleic acid as the absorption enhancers.
Figure 11:
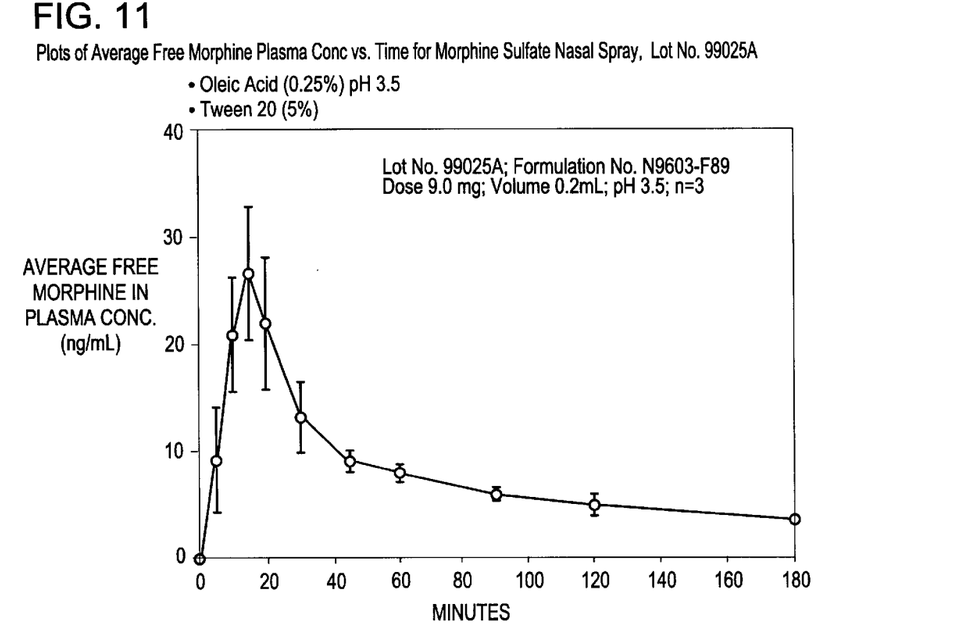
FIG. 11 is a graph showing the plasma concentrations of free morphine when morphine sulfate was administered by the intranasal route. The formulation was at a pH of 3.5 and included Tween 20 and oleic acid as the absorption enhancers.

Morphine Sulfate Formulations With Oleic Acid and Tween 20 Absorption Enhancers FIG. 10 is a graph showing the plasma concentrations of free morphine when 9.5 mg of morphine sulfate was administered to healthy volunteers by the intranasal route using Formulation 10 (Table J). This formulation was at a pH of 6.0 and included about 0.25% oleic acid and about 5% Tween 20 as the absorption enhancers. FIG. 11 is a graph showing the plasma concentrations of free morphine when 9.0 mg of morphine sulfate was administered to healthy volunteers by the intranasal route using Formulation 11 (Table K). This formulation was at a pH of 3.5 and included about 0.25% oleic acid and about 5% Tween 20 as the absorption enhancers. The average peak concentrations ($C_{MAX}$) concentrations for intranasal Formulations 10 and 11 was 31.9 ng/ml and 27.5 ng/ml, respectively. Referring to FIG. 10, use of 0.25% oleic acid and 5% Tween 20 enhanced the nasal absorption of morphine sulfate at a pH of 6.0 beyond that observed with Formulation 3, which includes 5% Tween 20 also at a pH of 6.0. Referring to FIG. 11, use of 0.25% oleic acid and 5% Tween 20 enhanced the nasal absorption of morphine sulfate at a pH of 3.5 beyond that observed with Formulation 3, which includes 5% Tween 20 at a pH of 6.0. These results were unexpected since morphine sulfate is predominately in its ionized state at pH 3.5 to 6.0 and therefore it is expected that the absorption would be poor. By contrast, we found substantial absorption at pH ranges 3.5 to 6.0 where the drug is predominately ionized.

EXAMPLE 8

Figure 12:
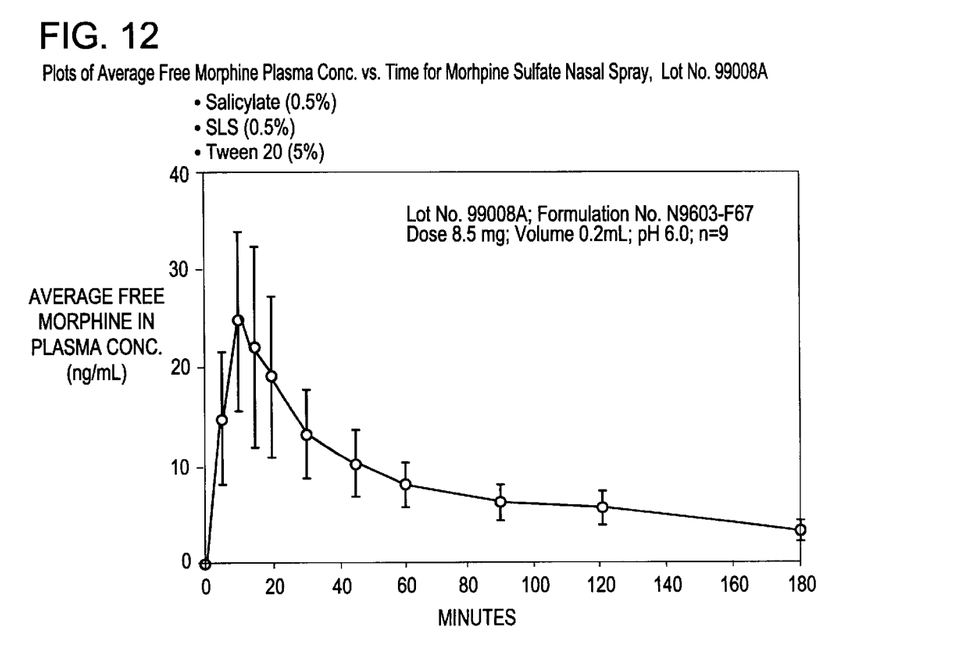
FIG. 12 is a graph showing the plasma concentrations of free morphine when morphine sulfate was administered by the intranasal route. The formulation was at a pH of 6.0 and included Tween 20, sodium salicylate and sodium lauryl sulfate as the absorption enhancers.
Figure 13:
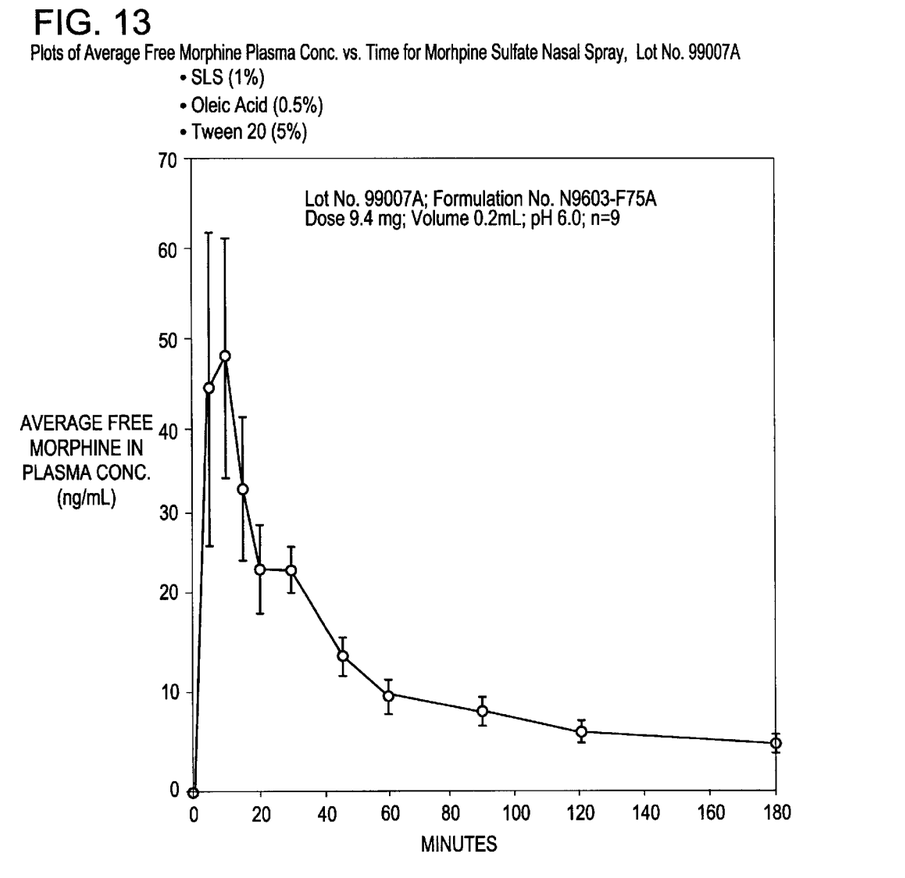
FIG. 13 is a graph showing the plasma concentrations of free morphine when morphine sulfate was administered by the intranasal route. The formulation was at a pH of 6.0 and included Tween 20, sodium salicylate and oleic acid as the absorption enhancers.

Morphine Sulfate Formulations With Sodium Lauryl Sulfate, Tween 20 and Oleic Acid or Sodium Salicylate Absorption Enhancers FIG. 12 is a graph showing the plasma concentrations of free morphine when 8.5 mg morphine sulfate was administered to healthy volunteers by the intranasal route using Formulation 12 (Table L). This formulation was at a pH of 6.0 and included about 5% Tween 20, about 0.5% sodium salicylate and 0.5% sodium lauryl sulfate as the absorption enhancers. FIG. 13 is a graph showing the plasma concentrations of free morphine when 9.4 mg morphine sulfate was administered to healthy volunteers by the intranasal route using Formulation 13 (Table M). This formulation was at a pH of 6.0 and included about 5% Tween 20, about 1% sodium lauryl sulfate and about 0.5% oleic acid as the absorption enhancers. The average peak concentrations ($C_{MAX}$) concentrations for intranasal Formulations 12 and 13 was 25.6 ng/ml and 51.7 ng/ml, respectively. Referring to FIG. 12, use of 0.5% sodium lauryl sulfate, 0.5% sodium salicylate and 5% Tween 20 enhanced the nasal absorption of morphine sulfate at a pH of 6.0 beyond that observed using 5% Tween 20 also at a pH of 6.0. Referring to FIG. 13, use of 1% sodium lauryl sulfate, 0.5% oleic acid and 5% Tween 20 enhanced the nasal absorption of morphine sulfate at a pH of 6 beyond that observed using 5% Tween 20, also at a pH of 6.0 (Formulation 3).

In summary, the above results were unexpected since morphine sulfate is predominately in its ionized state at pH 3.5 to 6.0 and therefore it is expected that the absorption would be poor. By contrast, we found substantial absorption at pH ranges 3.5 to 6.0 where the drug is predominately ionized. Also, the addition of the absorption enhancer, such as Tween 20, sodium lauryl sulfate, sodium salicylate, and oleic acid, increased intranasal absorption and peak plasma concentrations of morphine.

The invention being thus described, it will be obvious that the same may be varied in many ways. Such variations are not to be regarded as a departure from the spirit and scope of the invention and all such modifications are intended to be included within the scope of the following claims.

TABLE A

Morphine Sulfate Formulation 1 (Lot 98083A)

| # | Item | % Amount w/w |
|---|------|--------------|
| Batch Size = 100 g | | |
| pH = 4.0 | | |
| 1 | Morphine Sulfate, USP | 5 |
| 2 | Sodium Citrate Dihydrate, USP | 1.27 |
| 3 | Citric Acid Anhydrous, USP | 1.17 |
| 4 | Glycerin 96%, USP | 5.0 |
| 5 | Sodium Metabisulfite, NF | 0.10 |

TABLE A-continued

Morphine Sulfate Formulation 1 (Lot 98083A)

| # | Item | % Amount w/w |
|---|---|---|
| 6 | Benzalkonium Chloride, 50% solution, NF | 0.04 |
| 7 | Purified Water, USP QS to Batch Size | 100 |

TABLE B

Morphine Sulfate Formulation 2 (Lot 99002A)

| # | Item | % Amount w/w |
|---|---|---|
| \multicolumn{3}{l}{Batch Size = 100 g} | |
| \multicolumn{3}{l}{pH = 6.0} | |
| 1 | Morphine Sulfate, USP | 5 |
| 2 | Sodium Citrate Dihydrate, USP | 0.29 |
| 3 | Glycerin 96%, USP | 5.0 |
| 4 | Sodium Metabisulfite, NF | 0.10 |
| 5 | Benzalkonium Chloride, 50% solution, NF | 0.040 |
| 6 | Purified Water, USP QS to Batch Size | 100 |

TABLE C

Morphine Sulfate Formulation 3 (Lot 99020A & Lot 99024A)

| # | Item | % Amount w/w |
|---|---|---|
| Batch Size = 100 g | | |
| pH = 6.0 | | |
| 1 | Morphine Sulfate, USP | 4.5 |
| 2 | Polysorbate 20, NF (Tween 20) | 5.0 |
| 3 | Glycerin 96%, USP | 5.0 |
| 4 | Sodium Metabisulfite, NF | 0.10 |
| 5 | Edetate Disodium, USP | 0.075 |
| 6 | Trolamine, NF | TAP |
| 7 | Purified Water, USP QS to Batch Size | 100 |

TAP = To adjust pH

TABLE D

Morphine Sulfate Formulation 4 (Lot 99006A)

| # | Item | % Amount w/w |
|---|---|---|
| Batch Size = 100 g | | |
| pH = 6.0 | | |
| 1 | Morphine Sulfate, USP | 5.0 |
| 2 | Sodium Citrate Dihydrate, USP | 0.30 |
| 3 | Sodium Salicylate, USP | 1.0 |
| 4 | Glycerin 96%, USP | 5.0 |
| 5 | Sodium Metabisulfite, NF | 0.10 |
| 6 | Purified Water, USP QS to Batch Size | 100 |

TAP = To adjust pH

TABLE E

Morphine Sulfate Formulation 5 (Lot 99021A)

| # | Item | % Amount w/w |
|---|---|---|
| Batch Size = 100 g | | |
| pH = 6.0 | | |
| 1 | Morphine Sulfate, USP | 3.70 |
| 2 | Polyoxyl (40) Stearate, NF | 8.70 |
| 3 | Polysorbate 20, NF (Tween 20) | 8.70 |
| 4 | Glycerin 96%, USP | 8.70 |
| 5 | Sodium Metabisulfite, NF | 0.090 |
| 6 | Edetate Disodium, USP | 0.065 |
| 7 | Trolamine, NF | TAP |
| 8 | Purified Water, USP QS to Batch Size | 100 |

TAP = To adjust pH

TABLE F

Morphine Sulfate Formulation 6 (Lot 99028A)

| # | Item | % Amount w/w |
|---|---|---|
| Batch Size = 100 g | | |
| pH = 3.5 | | |
| 1 | Morphine Sulfate, USP | 10.0 |
| 2 | Glyceryl Monooleate (GRAS) | 5.0 |
| 3 | Polysorbate 20, NF (Tween 20) | 5.0 |
| 4 | Glycerin 96%, USP | 5.0 |
| 5 | Sulfuric Acid, NF | TAP |
| 6 | Purified Water, USP | 100 |

TAP = To adjust pH

TABLE G

Morphine Sulfate Formulation 7 (Lot 99029A)

| # | Item | % Amount w/w |
|---|---|---|
| Batch Size = 100 g | | |
| pH = 6.0 | | |
| 1 | Morphine Sulfate, USP | 10.0 |
| 2 | Glycerol Monooleate (GRAS) | 5.0 |
| 3 | Polysorbate 20, NF (Tween 20) | 5.0 |
| 4 | Glycerine 96%, USP | 5.0 |
| 5 | Trolamine, NF | TAP |
| 6 | Purified Water, USP | 100 |

TAP = To adjust pH

TABLE H

Morphine Sulfate Formulation 8 (Lot 99022A)

| # | Item | Amount w/w |
|---|---|---|
| Batch Size = 100 g | | |
| pH = 6.0 | | |
| 1 | Morphine Sulfate, USP | 4.45 |
| 2 | Lecithin, NF | 0.99 |
| 3 | Polysorbate, NF (Tween 20) | 4.95 |
| 4 | Sodium Metabisulfite, NF | 0.099 |
| 5 | Glycerin 96%, USP | 4.95 |
| 6 | Edetate Disodium, USP | 0.074 |

TABLE H-continued

Morphine Sulfate
Formulation 8
(Lot 99022A)

| # | Item | Amount w/w |
|---|---|---|
| 7 | Trolamine, NF | TAP |
| 8 | Purified Water, USP | 100 |

TAP = To adjust pH

TABLE I

Morphine Sulfate
Formulation 9
(Lot 99015A)

| # | Item | % Amount w/w |
|---|---|---|
| Batch Size = 100 g | | |
| pH = 6.0 | | |
| 1 | Morphine Sulfate, USP | 4.69 |
| 2 | Sodium Lauryl Sulfate, NF | 1.02 |
| 3 | Polysorbate 20, NF (Tween 20) | 5.10 |
| 4 | Sodium Metabisulfite, NF | 0.102 |
| 5 | Edetate Disodium, USP | 0.0765 |
| 6 | Trolamine, NF | TAP |
| 7 | Purified Water, USP | 100 |

TAP = To adjust pH

TABLE J

Morphine Sulfate
Formulation 10
(Lot 99014A)

| # | Item | % Amount w/w |
|---|---|---|
| Batch Size = 100 g | | |
| pH = 6.0 | | |
| 1 | Morphine Sulfate, USP | 4.72 |
| 2 | Oleic Acid, NF | 0.255 |
| 3 | Polysorbate 20, NF (Tween 20) | 5.10 |
| 4 | Sodium Metabisulfite, NF | 0.10 |
| 5 | Edetate Disodium, USP | 0.077 |
| 6 | Trolamine, NF | TAP |
| 7 | Purified Water, USP | 100 |

TAP = To adjust pH

TABLE K

Morphine Sulfate
Formulation 11
(Lot 99025A)

| # | Item | % Amount w/w Per Batch |
|---|---|---|
| Batch Size = 100 g | | |
| pH = 3.50 | | |
| 1 | Morphine Sulfate, USP | 4.47 |
| 2 | Oleic Acid, NF | 0.248 |
| 3 | Polysorbate 20, NF (Tween 20) | 4.98 |
| 4 | Glycerin 96%, USP | 4.98 |
| 5 | Sodium Metabisulfite, NF | 0.10 |
| 6 | Edetate Disodium, USP | 0.075 |
| 7 | Purified Water, USP | 100 |

TABLE L

Morphine Sulfate
Formulation 12
(Lot 99008A)

| # | Item | % Amount w/w |
|---|---|---|
| Batch Size = 100 g | | |
| pH = 6.0 | | |
| 1 | Morphine Sulfate, USP | 4.25 |
| 2 | Sodium Lauryl sulfate, NF | 0.50 |
| 3 | Sodium salicylate, USP | 0.50 |
| 4 | Polysorbate 20 (Tween 20) | 5.0 |
| 5 | Sodium Metabisulfite, NF | 0.10 |
| 6 | Edetate Disodium, USP | 0.075 |
| 7 | Trolamine, NF | TAP |
| 8 | Purified Water, USP | 100 |

TAP = To adjust pH

TABLE M

Morphine Sulfate
Formulation 13
(Lot 99007A)

| # | Item | % Amount |
|---|---|---|
| Batch Size = 100 g | | |
| pH = 6.0 | | |
| 1 | Morphine Sulfate, USP | 4.7 |
| 2 | Sodium Lauryl Sulfate, NF | 1.0 |
| 3 | Oleic Acid, NF | 0.50 |
| 4 | Polysorbate 20, NF (Tween 20) | 5.0 |
| 5 | Sodium Metabisulfite, NF | 0.10 |
| 6 | Edetate Disodium, USP | 0.075 |
| 7 | Trolamine, NF | TAP |
| 8 | Purified Water, USP | 100 |

TAP = To adjust pH

STRUCTURE A

What is claimed is:

1. A method for eliciting an analgesic or anesthetic response in a mammal in need thereof comprising nasally administering a therapeutically effective amount of morphine sulfate at a pH from 4.0 to 6.0, wherein said pH of the morphine sulfate is maintained with a buffer selected from the group consisting of acetate, citrate, prolamine, carbonate and phosphate and combination thereof.

2. A method for eliciting an analgesic or anesthetic response in a mammal in need thereof comprising nasally administering a therapeutically effective amount of morphine sulfate at a pH from 4.0 to 6.0 to the mammal in combination with a nasal delivery system, wherein said pH of the morphine sulfate is maintained with a buffer selected from the group consisting of acetate, citrate, prolamine, carbonate and phosphate and combination thereof.

3. A method according to claim 2, wherein the morphine sulfate is dispersed in an aqueous or non-aqueous formulation.

4. A method according to claim 3, wherein morphine sulfate is at a concentration below about 50% w/w.

5. A method according to claim 3, wherein morphine sulfate is at a concentration below about 10% w/w.

6. A method according to claim 3, wherein morphine sulfate is dispersed in suspensions, solutions, powders, gels, ointments and creams.

7. A method according to claim 2, wherein the nasal delivery system comprises a thickening agent, a humectant, an absorption enhancer and combinations thereof.

8. A method according to claim 7 further comprising one or more pharmaceutical excipients.

9. A method according to claim 7 further comprising a pharmaceutically acceptable preservative.

10. A method according to claim 7, wherein the thickening agent is selected from the group consisting of methyl cellulose, xanthan gum, carboxymethyl cellulose, hydroxypropyl cellulose, carbomer, polyvinyl alcohol, alginates, acacia, chitosan and combinations thereof.

11. A method according to claim 7, wherein the humectant is selected from the group consisting of sorbitol, glycerol, mineral oil, vegetable oil and combinations thereof.

12. A method according to claim 7, wherein the absorption enhancer is selected from the group consisting of sodium lauryl sulfate, sodium salicylate, oleic acid, lecithin, dehydrated alcohol, Tween, Span, polyoxyl 40 stearate, polyoxy ethylene 50 stearate, edetate disodium, propylene glycol, glycerol monooleate, fusieates, bile salts, octoxynol and combinations thereof.

13. A method according to claim 7, wherein the absorption enhancer is selected from the group of anionic, cationic and nonionic surfactants and combinations thereof.

* * * * *

UNITED STATES PATENT AND TRADEMARK OFFICE
CERTIFICATE OF CORRECTION

PATENT NO. : 6,677,346 B1
DATED : January 13, 2004
INVENTOR(S) : Achari et al.

It is certified that error appears in the above-identified patent and that said Letters Patent is hereby corrected as shown below:

Column 17,
Line 7, claim 7 should read
A method according to Claim 17, wherein the nasal delivery system comprises a buffer to maintain the pH of the morphine sulfate, a thickening agent, a humectant, an absorption enhancer and combinations thereof.

Column 18,
Line 8, "polyoxyethylene" is one word.

Signed and Sealed this

Twenty-seventh Day of July, 2004

JON W. DUDAS
*Acting Director of the United States Patent and Trademark Office*